United States Patent [19]

Scarborough

[11] Patent Number: 5,780,595
[45] Date of Patent: Jul. 14, 1998

[54] PLATELET AGGREGATION INHIBITORS

[75] Inventor: Robert M. Scarborough, Belmont, Calif.

[73] Assignee: COR Therapeutics, Inc., South San Francisco, Calif.

[21] Appl. No.: 460,869

[22] Filed: Jun. 5, 1995

Related U.S. Application Data

[63] Continuation of Ser. No. 806,558, Dec. 13, 1991, abandoned, which is a continuation-in-part of Ser. No. 586,610, Sep. 24, 1990, abandoned, which is a continuation-in-part of Ser. No. 542,488, Jun. 22, 1990, abandoned, which is a continuation-in-part of Ser. No. 483,229, Feb. 20, 1990, Pat. No. 5,318,899, which is a continuation-in-part of Ser. No. 418,028, Oct. 6, 1989, abandoned, which is a continuation-in-part of Ser. No. 367,509, Jun. 16, 1989, abandoned.

[51] Int. Cl.$^6$ .................................................... C07K 16/00
[52] U.S. Cl. ................ 530/387.9; 530/328; 530/388.1; 530/388.75; 530/389.1; 530/389.3
[58] Field of Search .................... 530/328, 387.9, 530/388.1, 388.25, 389.1, 389.3

[56] References Cited

U.S. PATENT DOCUMENTS

| | | |
|---|---|---|
| 4,517,686 | 5/1985 | Ruoslahti et al. . |
| 4,578,079 | 3/1986 | Ruoslahti et al. . |
| 4,589,881 | 5/1986 | Pierschbacher et al. . |
| 4,614,517 | 9/1986 | Ruoslahti et al. . |
| 4,652,639 | 3/1987 | Stabinsky . |
| 4,661,111 | 4/1987 | Ruoslahti et al. . |
| 4,661,471 | 4/1987 | Hawiger et al. .............. 514/13 |
| 4,683,291 | 7/1987 | Zimmerman et al. . |
| 4,792,525 | 12/1988 | Ruoslahti et al. . |
| 4,857,508 | 8/1989 | Adams et al. . |
| 4,992,463 | 2/1991 | Troeng et al. . |
| 5,023,233 | 6/1991 | Nutt . |
| 5,100,875 | 3/1992 | de Rotrou . |
| 5,318,899 | 6/1994 | Scarborough et al. ........... 435/69.6 |
| 5,338,723 | 8/1994 | Nutt . |
| 5,340,798 | 8/1994 | Nutt . |
| 5,344,783 | 9/1994 | Scarborough et al. ........... 436/501 |
| 5,374,622 | 12/1994 | Nutt . |

FOREIGN PATENT DOCUMENTS

| | | |
|---|---|---|
| 0 220 957 A2 | 10/1986 | European Pat. Off. . |
| 0 314 576 | 3/1987 | European Pat. Off. . |
| 0 298 820 | 5/1987 | European Pat. Off. . |
| 0 291 804 A2 | 5/1988 | European Pat. Off. . |
| 0 275 748 A1 | 7/1988 | European Pat. Off. . |
| 0 317 053 A2 | 8/1988 | European Pat. Off. . |
| 0 319 506 A2 | 12/1988 | European Pat. Off. . |
| 0 341 915 A2 | 5/1989 | European Pat. Off. . |
| 0 319 506 A2 | 6/1989 | European Pat. Off. . |
| 0 319 506 B1 | 6/1989 | European Pat. Off. . |
| 0 352 249 A1 | 7/1989 | European Pat. Off. . |
| 0 410 537 | 7/1990 | European Pat. Off. . |
| 0 410 539 | 7/1990 | European Pat. Off. . |
| 0 410 540 | 7/1990 | European Pat. Off. . |
| 0 410 541 A1 | 7/1990 | European Pat. Off. . |
| 0 410 767 | 7/1990 | European Pat. Off. . |
| 0 411 833 | 7/1990 | European Pat. Off. . |
| 0 382 451 A3 | 8/1990 | European Pat. Off. . |
| 0 422 938 A1 | 10/1990 | European Pat. Off. . |
| 0 425 212 A2 | 10/1990 | European Pat. Off. . |
| 0 406 428 | 1/1991 | European Pat. Off. . |
| 0 422 937 A1 | 4/1991 | European Pat. Off. . |
| 425212 | 5/1991 | European Pat. Off. . |
| 3 841 753 | 12/1988 | Germany . |
| 2-078631 | 3/1990 | Japan . |
| HEI 2/2990-78631 | 3/1990 | Japan . |
| 2 207 922 | 8/1987 | United Kingdom . |
| 88/03151 | 10/1987 | WIPO . |
| WO 89/07609 | 1/1989 | WIPO . |
| WO 89/05150 | 6/1989 | WIPO . |
| 00178 | 1/1990 | WIPO . |
| WO 90/06943 | 6/1990 | WIPO . |
| WO 90/08772 | 8/1990 | WIPO . |
| WO 91/04247 | 9/1990 | WIPO . |
| WO 91/05562 | 9/1990 | WIPO . |
| 15620 | 12/1990 | WIPO . |
| 90/15072 | 12/1990 | WIPO . |
| WO 91/11458 | 1/1991 | WIPO . |

OTHER PUBLICATIONS

Ali et al., *Structure–Activity studies Toward the Improvement of Antiaggregatory Activity of Arg–Gly–Asp–Ser (RGDS) Peptides: Chemistry, Structure and Biology* (Proceedings of the 11th American Peptide Symposium). Marshall, G.R. and River, J.E. editors, ESCOM, Leiden (1990) pp. 94–96.

Bennett et al., *Inhibition of Fibrinogen Binding Stimulated Human Platelets by a Monoclonal Antibody*, Proc. Natl. Acad. Sci., 80:2417–2421 (1983).

Cadroy et al., *RGDV Peptide Selectively Inhibits Platelet–Dependent Thrombus Formation In Vivo*, J. Clin. Invest., 84:939–944 (1989).

Chao et al., *Applaggin: A Potent Inhibitor of Platelet Aggregation and Secretion*, Thrombosis and Haemostasis 62(1):50, Abstract No. 120 (1989).

Chao et al., *Agkistrodon Piscivorus Piscivorus Platelet Aggregation Inhibitor: A Potent Inhibitor of Platelet Activation*, Pro. Natl. Acad. Sci., 86:8050–8054 (1989).

Dennis et al., *Platelet Glycoprotein IIb–IIIa Protein Antagonists from Snake Venoms: Evidence for a Family of Platelet–Aggregation Inhibitors*, Proc. Natl. Acad. Sci., 87:2471–2475 (1989).

Gan et al., *Echistatin, A Potent Platelet Aggregation Inhibitor from the Venom of the Viper, Echis Carinatus*, J. Biol. Chem., 263(36):19827–19832 (1988).

Garsky et al., *Chemical Synthesis of Echistatin, A Potent Inhibitor of Platelet Aggregation from Echis Carinatus: Synthesis and Biological Activity of Selected Analogs*, Proc. Natl. Acad. Sci., 86:4022–4026 (1989).

(List continued on next page.)

*Primary Examiner*—Sheela Huff
*Attorney, Agent, or Firm*—Cooley Godward LLP

[57] ABSTRACT

Peptides useful in inhibiting platelet aggregation are disclosed. These peptides contain the binding sequence Har-G-D and are disulfide-bridged cyclic compounds.

3 Claims, No Drawings

OTHER PUBLICATIONS

Huang et al., *Trigramin A Low Molecular Weight Peptide Inhibiting Fibrinogen Interaction with Platelet Receptor Expressed on Glycoprotein IIb–IIIa Complex*, J. Biol. Chem., 262(33):16157–16163 (1987).

Huang et al., *Trigramin: Primary Structure and Its Inhibition of von Willebrand Factor Binding to Glycoprotein IIb/IIIa Complex on Human Platelets*, Biochemistry, 28:661–666 (1989).

Huang et al., *Halysin, A Potent Platelet Aggregation Inhibitor, Inhibits the Fibrinogen Binding to the Activated Platelets*, Thrombosis and Haemostasis 62(1) :48, Abstract No. 112 (1989).

Kloczewiak et al., *Platelet Receptor Recognition Domain on the γChain of Human Fibrinogen and Its Synthetic Peptide Analogues*, Biochemistry, 28:2915–2919 (1989).

Knudsen et al., *Trigramin, an RGD–Containing Peptide from Snake Venom, Inhibits Cell–Sbustratum Adhesion of Human Melanoma Cells*, Exerimental Cell Research, 179:42–49 (1988).

Nachman et al., *Complex Formation of Platelet Membrane Glycoproteins IIb and IIIa with Fibrinogen*, Amer. Soc. for Clin. Invest., 69:263–269 (1982).

Niewiarowski et al., *Potential Application of RGD Containing Peptides from Viper Venoms (Disintegrins) in Antiplatelet Therapy*, Thrombosis and Haemostasis, 62(1):319, Abstract No. SY–XIV–5 (1989).

Phillips et al., *The Platelet Membrane Glycoprotein IIb–IIIa Complex*, Blood, 71:831–843 (1988).

Pierschbacher et al., *Influence of Stereochemistry of the Sequence Arg–Asp–Xaa on Binding Specificity in Cell Adhesion*, J. Biol. Chem., 262:17294–17298 (1987).

Pierschbacher and Ruoslahti, *Variants of the Cell Recognition Site of Fibronectin that Retain Attachment–Promoting Activity*, Proc. Natl. Acad. Sci., 81:5985–5988 (1984).

Plow et al., *Arginyl–Glycyl–Aspartic Acid Sequences and Fibrinogen Binding to Platelets*, Blood, 70(1):110–115 (1987).

Plow et al., *The Effect of Arg–Gly–Asp–containing peptides on Fibrinogen and von Willebrand Factor Binding to Platelets*, Proc. Natl. Acad. Sci., 82:8057–8061 (1985).

Niewiarowski et al., *Inhibition of Platelet Adhesion to Surfaces of Extracorporeal Circuit by RGD Containing Peptides from Viper Vemons*, Thrombosis and Haemostasis, 62:319, Abstract No. 853 (1989).

Ruggeri et al., *Inhibition of Platelet Function With Synthetic Peptides Designed to be High–Affinity Antagonists of Fibrinogen Binding to Platelets*; Proc. Natl. Acad. Sci. USA, 83:5708–5712 (1986).

Rucinski et al., *Batroxostatin, a RGD Containing Peptide from B. Atrox Venom, is a Potent Inhibitor of Cell Interaction with Adhesive Proteins*, Thrombosis and Haemostasis, 62:50, Abstract No. (1989).

Ruoslahti et al., *New Perspectives in Cell Adhesion: RGD and Integrins*, Science, 238:491–497 (1987).

Ruoslahti et al., *Arg–Gly–Asr: A Versatile Cell Recognition Signal*, Cell, 44:517–518 (1986).

Samanen et al., *An RGD–Peptide Analog with Potent Antithrombotic Activity In Vivo*, J. Cell. Biol. Supplement 14A:A229 (1990).

Shebuski et al., *Characterization and Platelet Inhibitory Activity of Bitistatin, a Potent Arginine–Glycine–Aspartic Acid Containing Peptide from the Venon of the Viper Bitis Arietans*, J. Biol. Chem., 264:21550–21556 (1989).

Timmons et al., *Antiplatelet "Hybrid" Peptide Analagous to Receptor Recognition Domains on γ and a α Chains of Human Fibrinogen*, Biochemistry, 28:2919–2923 (1989).

Tranqui et al., *Differential Structural Requirements for Fibrinogen Binding to Platelets and Endothelial Cells*, J. Cell Biol., 108:2519–2527 (1989).

Williams et al. *Inhibition of von Willebrand Factor Binding to Platelets by Two Recognition Site Peptides: The Pentadecapeptide of The Carboxy Terminus of the Fibrinogen Gamma Chain and the Terapeptide Arg–Gly–Asp–Ser*, Thrombosis Research, 46:457–471 (1987).

Williams et al., *Purification and Amino Acid Sequence of Two RGD–Containing Peptides from the Venoms of T. Elegans and T. Albolaris, Platelets*, FASEB Journal p. 310, Abstract No. 487.

Yasuda et al., *Monoclonal Antibody Against the Platelet Glycoprotein (GP) IIb/IIIa Receptor Prevents Coronary Artery Reocclusion After Reperfusion with Recombinant Tissue–Type Plasminogen Actvator in Dogs*, J. Clin. Invest. 81:1284–1291 (1988).

11th American Peptide Symposia, San Diego, California, Jul. 9–14, 1989.

Charon, et al., *Synthetic Peptide with Antithrombotic Activity*, Peptides, Chemistry, Structure and Biology, Proceedings of the Eleventh American Peptide Symposium, Jul. 9–14, 1989, La Jolla, CA. pp. 82–83.

Ginsberg, et al., *Inhibition of Fibronectin Binding to Platelets by Proteolytic Fragments and Synthetic Peptides Which Support Fibroblast Adhesion*, The Journal of Biological Chemistry, 260(7):3931–3936 (1985).

Hanson et al., *Baboon Models of Acute Arterial Thrombosis*, Thrombosis and Haemostatis, 58(3):801–805 (1987).

Hanson et al., *Platelet Interactions with Dacron Vascular Grafts*, Arteriosclerosis, 5:595–603 (Nov./ Dec. 1985).

Huang et al., *Mechanism of Action of the Platelet Aggregation Inhibitor Purified from Agkistrodon Halys (Mamushi) Snake Venom*, Toxicon, 22:243–252 (1984).

Huang et al., *Characterization of a Potent Platelet Aggregation Inhibitor from Agkistrodon Rhosodstoma Snake Venom*, Biochimica et Biophysica Acta 22789.925:248–257 (1987).

Kosugi et al., *Isolation of Platelet Aggregation Inhibitor from Trimeresurus Flavoviridis Snake Venom*, The Snake, 17:117–123 (1985).

Kumagai, et al., *Effect of Cyclic RGD Peptide On Cell Adhesion and Tumor Metastasis*, Biochemical and Biophysical Research Communications, 177(1)74–82 (1991).

Musial, et al., *Inhibition of Platelet Adhesion to Surfaces of Extracorporeal Circuits by Disintegrins*, Circulation, 82(1):262–273 (1990).

Nutt, et al., *Development of Novel, Highly Selective Fibrinogen Receptor Antagonists as Potentially Useful antithrombotic Agents*, Peptides, Chemistry and Biology, Proceedings of the Twelfth American Peptide Symposium, Jun. 16–21, 1991, Cambridge, MA. pp. 914–916.

Nutt, et al., *Structure– and Conformation–Activity Studies Leading to Potent Fibrinogen Receptor Antagonists Containing Arg–Gly–Asp*, Peptides, pp. 784–786 (1990).

Ouyang et al., *A Potent Platelet Aggregation Inhibitor Purified from Agkistrodon Halys (Mamushi) Snake Venom*, Toxicon, 21(6):797–804 (1983).

Samanen, et al., *Development of a Small RGD Peptide Fibrinogen Receptor Antagonist with Potent Antiaggregatory Activity in Vitro*. J. Med. Chem. 34:3114–3125 (1991).

Scarborough, *Design of Potent and Specific Integrin Antagonists*, J. Biol. Chem., 268:1066–1073 (1993).

Scarborough, et al., *Barbourin A GPIIb–IIIa–Specific Integrin Antagonist from the Venom of Sistrurus M. Barbouri*, The Journal of Biological Chemistry, 266(15):9359–9362 (1991).

Smith et al., *Table 3.1 The Structures of the α–amino Acids Commonly Found in Proteins*, Principles of Biochemistry, 7th Edition, pp. 32–33 (1983).

Steiner et al., $Ca^{2+}$–Dependent Binding of a Synthetic Arg–Gly–Asp–(RGD) Peptide to a Single Site on the Purified Platelet Glycoprotein IIb–IIIa Complex, J. Biol. Chem., 264(22):13102–13108 (1989).

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "Should be Mpr"

( i x ) FEATURE:
        ( A ) NAME/KEY: Modified-site
        ( B ) LOCATION: 3
        ( D ) OTHER INFORMATION: /note= "Should be Har"

( x i ) SEQUENCE DESCRIPTION: SEQ ID NO:1:

Xaa  Pro  Xaa  Gly  Asp  Trp  Pro  Cys
        1                          5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "Should be Mpr"

( i x ) FEATURE:
        ( A ) NAME/KEY: Modified-site (B) LOCATION: 3
                (D) OTHER INFORMATION: /note= "Should be Har"

(xi) SEQUENCE DESCRIPTION: SEQ ID NO:2:

Xaa  Gly  Xaa  Gly  Asp  Trp  Pro  Cys
                 1                  5

(2) INFORMATION FOR SEQ ID NO:3:

(i) SEQUENCE CHARACTERISTICS:
                (A) LENGTH: 8 amino acids
                (B) TYPE: amino acid
                (C) STRANDEDNESS: single
                (D) TOPOLOGY: linear (ix) FEATURE:
                (A) NAME/KEY: Modified-site
                (B) LOCATION: 1
                (D) OTHER INFORMATION: /note= "Should be Mpr"

(ix) FEATURE:
                (A) NAME/KEY: Modified-site
                (B) LOCATION: 3
                (D) OTHER INFORMATION: /note= "Should be Har"

(xi) SEQUENCE DESCRIPTION: SEQ ID NO:3:

Xaa  Ala  Xaa  Gly  Asp  Trp  Pro  Cys
                 1                  5

(2) INFORMATION FOR SEQ ID NO:4:

(i) SEQUENCE CHARACTERISTICS:
                (A) LENGTH: 8 amino acids
                (B) TYPE: amino acid
                (C) STRANDEDNESS: single
                (D) TOPOLOGY: linear (ix) FEATURE:
                (A) NAME/KEY: Modified-site
                (B) LOCATION: 1
                (D) OTHER INFORMATION: /note= "Should be Mpr"

(ix) FEATURE:
                (A) NAME/KEY: Modified-site
                (B) LOCATION: 2
                (D) OTHER INFORMATION: /note= "Should be Aib"

(ix) FEATURE:
                (A) NAME/KEY: Modified-site
                (B) LOCATION: 3
                (D) OTHER INFORMATION: /note= "Should be Har"

(xi) SEQUENCE DESCRIPTION: SEQ ID NO:4:

Xaa  Xaa  Xaa  Gly  Asp  Trp  Pro  Cys
                 1                  5

(2) INFORMATION FOR SEQ ID NO:5:

(i) SEQUENCE CHARACTERISTICS:
                (A) LENGTH: 8 amino acids
                (B) TYPE: amino acid
                (C) STRANDEDNESS: single
                (D) TOPOLOGY: linear (ix) FEATURE:
                (A) NAME/KEY: Modified-site
                (B) LOCATION: 1
                (D) OTHER INFORMATION: /note= "Should be Mpr"

(ix) FEATURE:
                (A) NAME/KEY: Modified-site
                (B) LOCATION: 2
                (D) OTHER INFORMATION: /note= "Should be N-Me-Arg"

-continued ( i x ) FEATURE:
    ( A ) NAME/KEY: Modified-site
    ( B ) LOCATION: 3
    ( D ) OTHER INFORMATION: /note= "Should be Har"

( x i ) SEQUENCE DESCRIPTION: SEQ ID NO:5:

Xaa Xaa Xaa Gly Asp Trp Pro Cys
    1                   5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "Should be Mpr"

( i x ) FEATURE:
        ( A ) NAME/KEY: Modified-site
        ( B ) LOCATION: 2
        ( D ) OTHER INFORMATION: /note= "Should be N-Me-Ser"

( i x ) FEATURE:
        ( A ) NAME/KEY: Modified-site
        ( B ) LOCATION: 3
        ( D ) OTHER INFORMATION: /note= "Should be Har"

( x i ) SEQUENCE DESCRIPTION: SEQ ID NO:6:

Xaa Xaa Xaa Gly Asp Trp Pro Cys
    1                   5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 3
        ( D ) OTHER INFORMATION: /note= "Should be Har"

( i x ) FEATURE:
        ( A ) NAME/KEY: Modified-site
        ( B ) LOCATION: 2
        ( D ) OTHER INFORMATION: /note= "Should be D-Ala"

( i x ) FEATURE:
        ( A ) NAME/KEY: Modified-site
        ( B ) LOCATION: 1
        ( D ) OTHER INFORMATION: /note= "Should be Mpr"

( x i ) SEQUENCE DESCRIPTION: SEQ ID NO:7:

Xaa Xaa Xaa Gly Asp Trp Pro Cys
    1                   5

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1

(D) OTHER INFORMATION: /note= "Should be Mpr"

(ix) FEATURE:
    (A) NAME/KEY: Modified-site
    (B) LOCATION: 2
    (D) OTHER INFORMATION: /note= "Should be bAla"

(ix) FEATURE:
    (A) NAME/KEY: Modified-site
    (B) LOCATION: 3
    (D) OTHER INFORMATION: /note= "Should be Har"

(xi) SEQUENCE DESCRIPTION: SEQ ID NO:8:

```
Xaa Xaa Xaa Gly Asp Trp Pro Cys
 1               5
```

(2) INFORMATION FOR SEQ ID NO:9:

(i) SEQUENCE CHARACTERISTICS:
    (A) LENGTH: 8 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note= "Should be Mpr"

(ix) FEATURE:
    (A) NAME/KEY: Modified-site
    (B) LOCATION: 2
    (D) OTHER INFORMATION: /note= "Should be N-Me-Leu"

(ix) FEATURE:
    (A) NAME/KEY: Modified-site
    (B) LOCATION: 3
    (D) OTHER INFORMATION: /note= "Should be Har"

(xi) SEQUENCE DESCRIPTION: SEQ ID NO:9:

```
Xaa Xaa Xaa Gly Asp Trp Pro Cys
 1               5
```

(2) INFORMATION FOR SEQ ID NO:10:

(i) SEQUENCE CHARACTERISTICS:
    (A) LENGTH: 8 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note= "Should be Mpr"

(ix) FEATURE:
    (A) NAME/KEY: Modified-site
    (B) LOCATION: 2
    (D) OTHER INFORMATION: /note= "Should be N-Me-Ala"

(ix) FEATURE:
    (A) NAME/KEY: Modified-site
    (B) LOCATION: 3
    (D) OTHER INFORMATION: /note= "Should be Har"

(xi) SEQUENCE DESCRIPTION: SEQ ID NO:10:

```
Xaa Xaa Xaa Gly Asp Trp Pro Cys
 1               5
```

(2) INFORMATION FOR SEQ ID NO:11:

(i) SEQUENCE CHARACTERISTICS:
    (A) LENGTH: 8 amino acids (B) TYPE: amino acid
(C) STRANDEDNESS: single
(D) TOPOLOGY: linear (ix) FEATURE:
    (A) NAME/KEY: Modified-site
    (B) LOCATION: 1
    (D) OTHER INFORMATION: /note= "Should be Mpr"

(ix) FEATURE:
    (A) NAME/KEY: Modified-site
    (B) LOCATION: 2
    (D) OTHER INFORMATION: /note= "Should be Sar"

(ix) FEATURE:
    (A) NAME/KEY: Modified-site
    (B) LOCATION: 3
    (D) OTHER INFORMATION: /note= "Should be Har"

(xi) SEQUENCE DESCRIPTION: SEQ ID NO:11:

```
Xaa Xaa Xaa Gly Asp Trp Pro Cys
 1               5
```

(2) INFORMATION FOR SEQ ID NO:12:

(i) SEQUENCE CHARACTERISTICS:
    (A) LENGTH: 8 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note= "Should be Mpr"

(ix) FEATURE:
    (A) NAME/KEY: Modified-site
    (B) LOCATION: 3
    (D) OTHER INFORMATION: /note= "Should be Har"

(xi) SEQUENCE DESCRIPTION: SEQ ID NO:12:

```
Xaa Val Xaa Gly Asp Trp Pro Cys
 1               5
```

(2) INFORMATION FOR SEQ ID NO:13:

(i) SEQUENCE CHARACTERISTICS:
    (A) LENGTH: 8 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note= "Should be Mpr"

(ix) FEATURE:
    (A) NAME/KEY: Modified-site
    (B) LOCATION: 3
    (D) OTHER INFORMATION: /note= "Should be Har"

(xi) SEQUENCE DESCRIPTION: SEQ ID NO:13:

```
Xaa Ser Xaa Gly Asp Trp Pro Cys
 1               5
```

(2) INFORMATION FOR SEQ ID NO:14:

(i) SEQUENCE CHARACTERISTICS:
    (A) LENGTH: 8 amino acids
    (B) TYPE: amino acid
    (C) STRANDEDNESS: single
    (D) TOPOLOGY: linear, ( i x ) FEATURE:
    ( A ) NAME/KEY: Modified-site
    ( B ) LOCATION: 1
    ( D ) OTHER INFORMATION: /note= "Should be Mpr"

( i x ) FEATURE:
    ( A ) NAME/KEY: Modified-site
    ( B ) LOCATION: 2
    ( D ) OTHER INFORMATION: /note= "Should be Har"

( x i ) SEQUENCE DESCRIPTION: SEQ ID NO:14:

Xaa Xaa Gly Asp Trp Pro Ala Cys
    1               5

( 2 ) INFORMATION FOR SEQ ID NO:15:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note= "Should be Mpr"

( i x ) FEATURE:
    ( A ) NAME/KEY: Modified-site
    ( B ) LOCATION: 2
    ( D ) OTHER INFORMATION: /note= "Should be Har"

( i x ) FEATURE:
    ( A ) NAME/KEY: Modified-site
    ( B ) LOCATION: 7
    ( C ) OTHER INFORMATION: /note= "Should be N-Me-Ala"

( x i ) SEQUENCE DESCRIPTION: SEQ ID NO:15:

Xaa Xaa Gly Asp Trp Pro Xaa Cys
    1               5

( 2 ) INFORMATION FOR SEQ ID NO:16:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note= "Should be Mpr"

( i x ) FEATURE:
    ( A ) NAME/KEY: Modified-site
    ( B ) LOCATION: 2
    ( D ) OTHER INFORMATION: /note= "Should be Har"

( x i ) SEQUENCE DESCRIPTION: SEQ ID NO:16:

Xaa Xaa Gly Asp Trp Pro Gly Cys
    1               5

( 2 ) INFORMATION FOR SEQ ID NO:17:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i x ) FEATURE:
    ( A ) NAME/KEY: Modified-site ( B ) LOCATION: 1
( D ) OTHER INFORMATION: /note= "Should be Mpr"

( i x ) FEATURE:
( A ) NAME/KEY: Modified-site
( B ) LOCATION: 2
( D ) OTHER INFORMATION: /note= "Should be Har"

( i x ) FEATURE:
( A ) NAME/KEY: Modified-site
( B ) LOCATION: 7
( c ) OTHER INFORMATION: /note= "Should be D-Ala"

( x i ) SEQUENCE DESCRIPTION: SEQ ID NO:17:

Xaa Xaa Gly Asp Trp Pro Xaa Cys
1                   5

( 2 ) INFORMATION FOR SEQ ID NO:18:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note= "Should be Mpr"

( i x ) FEATURE:
( A ) NAME/KEY: Modified-site
( B ) LOCATION: 2
( D ) OTHER INFORMATION: /note= "Should be Har"

( x i ) SEQUENCE DESCRIPTION: SEQ ID NO:18:

Xaa Xaa Gly Asp Trp Pro Pro Cys
1                   5

( 2 ) INFORMATION FOR SEQ ID NO:19:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note= "Should be Mpr"

( i x ) FEATURE:
( A ) NAME/KEY: Modified-site
( B ) LOCATION: 2
( D ) OTHER INFORMATION: /note= "Should be Har"

( i x ) FEATURE:
( A ) NAME/KEY: Modified-site
( B ) LOCATION: 7
( D ) OTHER INFORMATION: /note= "Should be Sar"

( x i ) SEQUENCE DESCRIPTION: SEQ ID NO:19:

Xaa Xaa Gly Asp Trp Pro Xaa Cys
1                   5

( 2 ) INFORMATION FOR SEQ ID NO:20:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i x ) FEATURE:
        ( A ) NAME/KEY: Modified-site
        ( B ) LOCATION: 1
        ( D ) OTHER INFORMATION: /note= "Should be Mpr"

( i x ) FEATURE:
        ( A ) NAME/KEY: Modified-site
        ( B ) LOCATION: 2
        ( D ) OTHER INFORMATION: /note= "Should be Har"

( i x ) FEATURE:
        ( A ) NAME/KEY: Modified-site
        ( B ) LOCATION: 7
        ( D ) OTHER INFORMATION: /note= "Should be Aib"

( x i ) SEQUENCE DESCRIPTION: SEQ ID NO:20:

```
Xaa Xaa Gly Asp Trp Pro Xaa Cys
 1               5
```

( 2 ) INFORMATION FOR SEQ ID NO:21:

( i ) SEQUENCE CHARACTERISTICS:
          ( A ) LENGTH: 8 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 1
          ( D ) OTHER INFORMATION: /note= "Should be Mpr"

( i x ) FEATURE:
          ( A ) NAME/KEY: Modified-site
          ( B ) LOCATION: 3
          ( D ) OTHER INFORMATION: /note= "Should be Har"

( i x ) FEATURE:
          ( A ) NAME/KEY: Modified-site
          ( B ) LOCATION: 8
          ( D ) OTHER INFORMATION: /note= "Should be Pen"

( x i ) SEQUENCE DESCRIPTION: SEQ ID NO:21:

```
Xaa Ala Xaa Gly Asp Trp Pro Xaa
 1               5
```

( 2 ) INFORMATION FOR SEQ ID NO:22:

( i ) SEQUENCE CHARACTERISTICS:
          ( A ) LENGTH: 8 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 1
          ( D ) OTHER INFORMATION: /note= "Should be Mpr"

( i x ) FEATURE:
          ( A ) NAME/KEY: Modified-site
          ( B ) LOCATION: 8
          ( D ) OTHER INFORMATION: /note= "Should be Pen"

( x i ) SEQUENCE DESCRIPTION: SEQ ID NO:22:

```
Xaa Ala Lys Gly Asp Trp Pro Xaa
 1               5
```

( 2 ) INFORMATION FOR SEQ ID NO:23:

( i ) SEQUENCE CHARACTERISTICS:
          ( A ) LENGTH: 8 amino acids
          ( B ) TYPE: amino acid
          ( C ) STRANDEDNESS: single -continued

```
        ( D ) TOPOLOGY: linear ( i x ) FEATURE:
        ( A ) NAME/KEY: Modified-site
        ( B ) LOCATION: 1
        ( D ) OTHER INFORMATION: /note= "Should be Mpr"

( i x ) FEATURE:
        ( A ) NAME/KEY: Modified-site
        ( B ) LOCATION: 3
        ( D ) OTHER INFORMATION: /note= "Should be Har"

( i x ) FEATURE:
        ( A ) NAME/KEY: Modified-site
        ( B ) LOCATION: 8
        ( D ) OTHER INFORMATION: /note= "Should be Pen"

( x i ) SEQUENCE DESCRIPTION: SEQ ID NO:23:

Xaa  Asp  Xaa  Gly  Asp  Trp  Pro  Xaa
    1                   5
```

PLATELET AGGREGATION INHIBITORS

CROSS-REFERENCE TO RELATED APPLICATIONS

This application is a continuation of U.S. Ser. No. 07/806,558, filed Dec. 13,1991, now abandoned, which is a continuation-in-part of Ser. No. 07/586,610, filed Sep. 24, 1990, now abandoned, which is a continuation-in-part of Ser. No. 07/542,488, filed Jun. 22, 1990, now abandoned, which is a continuation-in-part of Ser. No. 07/483,229, filed Feb. 20, 1990, now U.S. Pat. No. 5,318,899, which is a continuation-in-part of Ser. No. 07/418,028, filed Oct. 6, 1989, now abandoned, which is a continuation-in-part of 07/367,509, filed Jun. 16, 1989, now abandoned.

TECHNICAL FIELD

This invention relates to a group of peptides which are, or are related to, platelet aggregation inhibitors isolated and purified from various snake venoms. These peptides are useful as therapeutic agents for the treatment of, and prevention of, platelet-associated ischemic disorders. More specifically, the invention concerns peptides which block specific receptors for adhesive proteins involved in platelet adherence and aggregation.

BACKGROUND ART

Heart disease is the primary cause of death in most western societies. Death from heart disease is often induced by platelet-dependent ischemic syndromes which are initiated by atherosclerosis and arteriosclerosis and include, but are not limited to, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet activation either on vessel walls or within the lumen by blood-borne mediators but are manifested by platelet aggregates which form thrombi that restrict blood flow.

Platelet aggregation is mediated by GP IIb-IIIa complex on the platelet membrane surface. GP IIb-IIIa exists on the surface of unstimulated platelets in an inactive form. When platelets are activated by adhesion and the physiological agonists, the GP IIb-IIIa also becomes activated such that it becomes a receptor for fibrinogen (Fg), von Willebrand Factor (vWF), and fibronectin (Fn) (see Phillips et al., *Blood* (1988) 71:831-843); however, it is the binding of fibrinogen and/ or von Willebrand factor that is believed to be principally responsible for platelet aggregation and thrombus formation in vivo. Therefore, substances which specifically inhibit the binding of fibrinogen or von Willebrand factor to GP IIb-IIIa inhibit platelet aggregation and could be candidates for inhibiting thrombus formation in vivo.

Several classes of peptides have been disclosed which block the binding of adhesive proteins to activated platelets and inhibit platelet aggregation. A summary of some of this art is published in WO90/15620, published 27 Dec. 1990. This published application also discloses a group of cyclic peptides which inhibit platelet aggregation selectively, and which are characterized by the adhesive sequence K*-G/Sar-D, wherein K* is a substituted or unsubstituted lysyl residue. The present invention provides additional members of this class.

DISCLOSURE OF THE INVENTION

The invention relates to members of a group of platelet aggregation inhibitors which are of the formula:

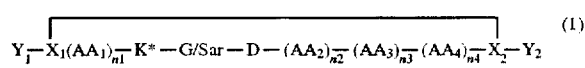

wherein K* is a substituted or unsubstituted lysyl residue of the formula $R^1_2N(CH_2)_4$ CHNHCO— as described above, wherein each $R^1$ is independently H, alkyl (1–6C), or at most one $R^1$ is $R^2$–C=NR$^3$, wherein $R^2$ is H, alkyl(1–6C) or is a substituted or unsubstituted phenyl or benzyl residue, or is $NR^4_2$ in which each $R^4$ is independently H or alkyl(1–6C), and $R^3$ is H, alkyl(1–6C), phenyl or benzyl, or $R^2$–C=NR$^3$ is a radical selected from the group consisting of:

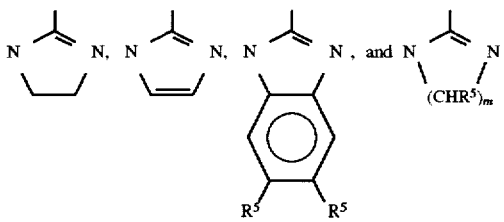

where m is an integer of 2–3, and each $R^5$ is independently H or alkyl(1–6C);

and wherein one or two ($CH_2$) may be replaced by O or S provided said O or S is not adjacent to another heteroatom;

$AA_1$ is a small, neutral (polar or nonpolar) amino acid and n1 is an integer of 0–3;

$AA_2$ is a neutral, nonpolar large (aromatic or nonaromatic) or a polar aromatic amino acid and n2 is an integer of 0–3;

$AA_3$ is a proline residue or a modified proline residue (as defined below) and n3 is an integer of 0–1;

$AA_4$ is a neutral, small amino acid or the N-alkylated form thereof and $n_4$ is an integer of 0–3;

each of $X_1$ and $X_2$ is independently a residue capable of forming a bond between $X_1$ and $X_2$ to obtain a cyclic compound as shown; and each of $Y_1$ and $Y_2$ is independently a noninterfering substituent or may be absent;

wherein one or more peptide linkages may optionally be replaced by a linkage selected from the group consisting of —$CH_2NH$—, —$CH_2S$—, $CH_2CH_2$—, —CH=CH— (cis and trans), —$COCH_2$—, —CH(OH)$CH_2$— and —$CH_2SO$—;

with the proviso that if n3 is 0; either:

1) the sum of n2 and n4 must be at least 2; or

2) K* must be other than Har or K; or

3) $X_2$ must be other than cys (C), penicillamine (Pen), or 2-amino-3,3-cyclopentanemethylene-3-mercaptopropionic acid (APmp); or 4) $Y_1$ or $Y_2$ must comprise at least one amino acid residue; or 5) one or more peptide linkages is replaced by said alternate linkage.

This invention concerns, specifically, compounds of the following formulas. Although all of these are capable of provision in cyclic form through formation of disulfide linkages, these linkages are not specifically shown.

| | |
|---|---|
| PAI 80 SEQ ID NO: 1 | Mpr-P-Har-G-D-W-P-C-NH$_2$ |
| PAI 81 SEQ ID NO: 2 | Mpr-G-Har-G-D-W-P-C-NH$_2$ |
| PAI 82 SEQ ID NO: 3 | Mpr-A-Har-G-D-W-P-C-NH$_2$ |
| PAI 83 SEQ ID NO: 4 | Mpr-Aib-Har-G-D-W-P-C-NH$_2$ |
| PAI 84 SEQ ID NO: 5 | Mpr-(N-Me-Arg)-Har-G-D-W-P-C-NH$_2$ |
| PAI 85 SEQ ID NO: 6 | Mpr-(N-Me-Ser)-Har-G-D-W-P-C-NH$_2$ |
| PAI 86 SEQ ID NO: 7 | Mpr-D-alanine-Har-G-D-W-P-C-NH$_2$ |
| PAI 87 SEQ ID NO: 8 | Mpr-(β-Ala)-Har-G-D-W-P-C-NH$_2$ |
| PAI 88 SEQ ID NO: 9 | Mpr-(N-Me-Leu)-Har-G-D-W-P-C-NH$_2$ |
| PAI 89 SEQ ID NO: 10 | Mpr-(N-Me-Ala)-Har-G-D-W-P-C-NH$_2$ |
| PAI 90 SEQ ID NO: 11 | Mpr-Sar-Har-G-D-W-P-C-NH$_2$ |
| PAI 91 SEQ ID NO: 12 | Mpr-V-Har-G-D-W-P-C-NH$_2$ |
| PAI 92 SEQ ID NO: 13 | Mpr-S-Har-G-D-W-P-C-NH$_2$ |
| PAI 93 SEQ ID NO: 14 | Mpr-Har-G-D-W-P-A-C-NH$_2$ |
| PAI 94 SEQ ID NO: 15 | Mpr-Har-G-D-W-P-(N-Me-Ala)-C-NH$_2$ |
| PAI 95 SEQ ID NO: 16 | Mpr-Har-G-D-W-P-G-C-NH$_2$ |
| PAI 96 SEQ ID NO: 17 | Mpr-Har-G-D-W-P-A$^{\dagger}$-C-NH$_2$ |
| PAI 97 SEQ ID NO: 18 | Mpr-Har-G-D-W-P-P-C-NH$_2$ |
| PAI 98 SEQ ID NO: 19 | Mpr-Har-G-D-W-P-(Sar)-C-NH$_2$ |
| PAI 99 SEQ ID NO: 20 | Mpr-Har-G-D-W-P-(Aib)-Cys-NH$_2$ |
| PAI 100 SEQ ID NO: 21 | Mpr-A-(Har)-G-D-W-P-Pen-NH$_2$ |
| PAI 101 SEQ ID NO: 22 | Mpr-A-K-G-D-W-P-Pen-NH$_2$ |
| PAI 102 SEQ ID NO: 23 | Mpr-D-(Har)-G-D-W-P-Pen-NH$_2$ |

The invention also concerns pharmaceutical compositions containing the peptides of the invention and methods to inhibit platelet aggregation using these peptides and formulations.

MODES OF CARRYING OUT THE INVENTION

The invention peptides can be synthesized and tested according to the methods described in WO90/15620, published 27 Dec. 1990 and incorporated herein by reference. Furthermore, antibodies may be prepared to these peptides as set forth therein. Briefly, compounds within the scope of the present invention can be synthesized chemically by means well known in the art such as, e.g., solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups such as fluorenylmethyloxycarbonyl (Fmoc), are suitable. For example, Boc-Gly-OH, Boc-Ala-OH, Boc-His (Tos)-OH, (i.e., selected carboxy-terminal amino acids) can be esterified to chloromethylated polystyrene resin supports, p-methyl benzhydrylamine (pMBHA) or PAM resins. The polystyrene resin support is preferably a copolymer of styrene with about 0.5 to 2% divinyl benzene as a cross-linking agent which causes the polystyrene polymer to be completely insoluble in certain organic solvents. See Stewart, et al., *Solid-Phase Peptide Synthesis* (1969) W. H. Freeman Co., San Francisco and Merrifield, *J Am Chem Soc* (1963) 85:2149–2154. These and other methods of peptide synthesis are also exemplified by U.S. Pat. Nos. 3,862,925, 3,842,067, 3,972,859, and 4,105,602.

The synthesis may use manual synthesis techniques or automatically employ, for example, an Applied BioSystems 430A or 431A Peptide Synthesizer (Foster City, Calif.) following the instructions provided in the instruction manual supplied by the manufacturer. Cleavage of the peptides from the resin can be performed using the "low-high" HF deprotection protocols as described in Lu, G.-S., et al., *Int J Peptide & Protein Res* (1987) 29:545–557. Refolding of analogs of the snake venom PAIs can be performed using the procedure outlined in Garsky, V., et al., *Proc Natl Acad Sci USA* (1989) 86:4022–4026 which describes the solid-phase synthesis of echistatin.

It will be readily appreciated by those having ordinary skill in the art of peptide synthesis that the intermediates which are constructed in accordance with the present disclosure during the course of synthesizing the present analog compounds are themselves novel and useful compounds and are thus within the scope of the invention.

Alternatively, selected compounds of the present invention can be produced by expression of recombinant DNA constructs prepared in accordance with well-known methods. Such production can be desirable to provide large quantities or alternative embodiments of such compounds. Since the peptide sequences are relatively short, recombinant production is facilitated; however, production by recombinant means is particularly preferred over standard solid phase peptide synthesis for peptides of at least 8 amino acid residues.

ANTIBODIES

Antibodies to the compounds of the invention may be prepared by standard immunization protocols involving administering these compounds to various vertebrates, such as rabbits, rats, mice, sheep, and chickens result in antisera which are immunoreactive with the purified peptide. The compounds of the invention may be advantageously conjugated to a suitable antigenically neutral carrier, such as an appropriate serum albumin or keyhole limpet hemocyanin, in order to enhance immunogenicity. In addition, the free peptide can be injected with methylated BSA as an alternative to conjugation. Furthermore, the antibody-secreting cells of the immunized mammal can be immortalized to generate monoclonal antibody panels which can then be screened for reactivity with the peptides.

The resulting polyclonal or monoclonal antibody preparations are useful in assays for levels of the corresponding peptides in biological samples using standard immunoassay procedures.

ASSAYS

The compounds of the invention are tested for platelet aggregation inhibition (PAI) activity using an assay performed as follows. GP IIb-IIIa, prepared in purified form, for example as described by Fitzgerald, L. A., et al., *Anal Biochem* (1985) 151:169–177, incorporated herein by reference, is coated onto a solid support such as beads, test tubes, or microtiter plates. The coated support is then contacted with fibrinogen and with the test material and incubated for a sufficient time to permit maximal binding of fibrinogen to the immobilized GP IIb-IIIa. Fibrinogen is typically provided at a concentration of about 5–50 nM and the test material can, if desired, be added at a series of dilutions. Typical incubations are 2–4 hr at 35° C., the time and temperature being interdependent.

After incubation, the solution containing the fibrinogen and test material is removed and the level of binding of fibrinogen measured by quantitating bound fibrinogen to GP IIb-IIIa. Any suitable means of detection may be used, but it is convenient to employ labeled fibrinogen, for example using radioactive, fluorescent or biotinylated labels. Such methods are well known and need not be elaborated here.

Assessment of the results is aided by employing a control sample, usually identical to the test sample except that the test substance is absent. In this case, percent inhibition may be calculated using the amount of Fg bound in the control as representing the basis, so that $$\% \text{ inhibition} = \frac{\text{control} - \text{test}}{\text{control}} \times 100.$$

Other measures of inhibition effectiveness, such as $IC_{50}$, may also be used.

The assay systems of the invention further include characterization of the PAI specificity by binding inhibition assays identical to that above but substituting other adhesive proteins for Fg and other receptors for GP IIb-IIIa. In particular, inhibition of the binding of vitronectin to the vitronectin receptor; fibronectin to the fibronectin receptor; fibronectin to GP IIb-IIIa and fibrinogen and/or vWF to GP IIb-IIIa may be assessed. The adhesive protein and receptors for these assays are available in the art.

In addition to the plate assays of the invention, other assays for platelet aggregation inhibition activity and related activities are also available, as set forth above. In summary, a list of commonly employed assays is as follows:

1. The plate assays utilizing specific receptors described in the previous paragraphs;
2. Standard assays directly applied to platelet aggregation, such as those described by Gann, Z.-R., et al., *J Biol Chem* (1988) 263:19827–19832; Huang, T. F., et al., *J Biol Chem* (1987) 262:16157–16163; *Biochemistry* (1989) 28:661–666, cited above and incorporated herein by reference;
3. An in vivo thrombosis model in dogs as described hereinbelow in Example 1, and by Folts, J. D., et al., *Circulation* (1976) 54:365; and
4. Effect on cell adhesion using S35 methionine-labeled cells as described hereinbelow in Example 19.

ADMINISTRATION AND UTILITY

The PAIs of the invention are useful therapeutically to prevent thrombus formation. Indications appropriate to such treatment include, without limitation, atherosclerosis and arteriosclerosis, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet activation oh vessel walls.

The PAIs may be used for prevention or abortion of arterial thrombus formation, in unstable angina and arterial emboli or thrombosis, as well as treatment or prevention of myocardial infarction (MI) and mural thrombus formation post MI. For brain-related disorders, treatment or prevention of transient ischemic attack and treatment of thrombotic stroke or stroke-in-evolution are included.

The PAIs may also be used for prevention of platelet aggregation, embolization, or consumption in extracorporeal circulations, including improving renal dialysis, cardiopulmonary bypasses, hemoperfusions, and plasmapheresis.

PAIs prevent platelet aggregation, embolization, or consumption associated with intravascular devices, and administration results in improved utility of intraaortic balloon pumps, ventricular assist devices, and arterial catheters.

The PAIs will also be useful in treatment or prevention of venous thrombosis as in deep venous thrombosis, IVC, renal vein or portal vein thrombosis, and pulmonary venous thrombosis.

Various disorders involving platelet consumption, such as thrombotic thrombocytopenic purpura are also treatable.

In addition, the PAIs of the present invention may be used in numerous nontherapeutic applications where inhibiting platelet aggregation is desired. For example, improved platelet and whole blood storage can be obtained by adding sufficient quantities of the peptides, the amount of which will vary depending upon the length of proposed storage time, the conditions of storage, the ultimate use of the stored material, etc.

The PAI dosage can range broadly depending upon the desired affects and the therapeutic setting. Typically, dosages will be between about 0.01 and 10 mg/kg, preferably between about 0.01 to 0.1 mg/kg, body weight. Administration is preferably parenteral, such as intravenous on a daily basis for up to a week or as much as one or two months or more, all of which will vary with the peptide's size. If the peptides are sufficiently small (e.g., less than about 8–10 amino acid residues) other routes of administration can be utilized, such as intranasally, sublingually, or the like.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

PREPARATION A

Preparation of G-C-G-K-G-D-W-P-C-A-NH$_2$

One-half mmol of PMBHA resin (0.72 meq/g, Applied Biosystems, Foster City, Calif.) was subjected to Procedure A with the required amino acids (introduced in order). The Boc-protected amino acids had the following side-chain protection: Asp(O-cHex), Cys(4-MeBzl), and Lys(Cl-Z). Following completion of the assembly of the protected peptide-resin, the amino terminal Boc group was removed with TFA and the resin dried as its TFA-salt form. The resin (1.54 g) was treated with anhydrous hydrogen fluoride (HF) containing 10% anisole, 2% ethyl methyl sulfide for 30 min at $-10°$ C., and an additional 30 min at $0°$ C. The HF was removed in vacuo and the peptide/resin mixture was suspended in diethyl ether followed by alternately washing with chloroform and ether 3X. After a final ether wash, the peptide was extracted from the resin with 2.1M acetic acid, diluted with distilled water and lyophilized.

The crude peptide (370 mg) was dissolved in deoxygenated 10 mM NH$_4$OAc, pH 8, to 0.5 mg/ml and allowed to oxidize by dropwise addition of a slight excess of 0.01M potassium ferricyanide (K$_3$Fe(CN)$_6$) solution, stirred an additional 20 min, and adjusted to pH 5 with acetic acid. The peptide solution was treated with DOWEX AG3×4 anion-exchange resin for 15 min with stirring and the resin filtered, diluted with H$_2$O and lyophilized to yield the crude cyclized peptide. The crude cyclized peptide (392 mg) was purified by desalting on Sephadex G-25F using 0.5M acetic acid as eluent, followed by ion-exchange chromatography on CM-Sepharose (Pharmacia) using an elution gradient generated by addition of 100 mM NH$_4$OAc to a solution of 10 mM NH$_4$OAc, pH 4.5. Fractions which had a minimum purity of 90% by HPLC analysis were pooled and lyophilized from H$_2$O several time to yield 175 mg. Final purification consisted of preparative HPLC purification on a Water C-18 reverse-phase column with an acetonitrile/water/TFA gradient to yield purified peptide.

EXAMPLE 1

Preparation of Additional Analogs

The following analogs were synthesized in a manner similar to that set forth in Preparation A and were tested for PAI activity in the assay method described hereinabove.

| Analog | Sequence | Appr. $IC_{50}$ (μM) |
|---|---|---|
| PAI 80 SEQ ID NO: 1 | Mpr-P-Har-G-D-W-P-C-NH$_2$ | 1.29 |
| PAI 81 SEQ ID NO: 2 | Mpr-G-Har-G-D-W-P-C-NH$_2$ | 7.47 |
| PAI 82 SEQ ID NO: 3 | Mpr-A-Har-G-D-W-P-C-NH$_2$ | 0.12 |
| PAI 83 SEQ ID NO: 4 | Mpr-Aib-Har-G-D-W-P-C-NH$_2$ | 2.20 |
| PAI 84 SEQ ID NO: 5 | Mpr-(N-Me-Arg)-Har-G-D-W-P-C-NH$_2$ | 0.25 |
| PAI 85 SEQ ID NO: 6 | Mpr-(N-Me-Ser)-Har-G-D-W-P-C-NH$_2$ | 0.28 |
| PAI 86 SEQ ID NO: 7 | Mpr-D-alanine-Har-G-D-W-P-C-NH$_2$ | 1.15 |
| PAI 87 SEQ ID NO: 8 | Mpr-(β-Ala)-Har-G-D-W-P-C-NH$_2$ | 0.92 |
| PAI 88 SEQ ID NO: 9 | Mpr-(N-Me-Leu)-Har-G-D-W-P-C-NH$_2$ | 0.84 |
| PAI 89 SEQ ID NO: 10 | Mpr-(N-Me-Ala)-Har-G-D-W-P-C-NH$_2$ | 0.62 |
| PAI 90 SEQ ID NO: 11 | Mpr-Sar-Har-G-D-W-P-C-NH$_2$ | 0.27 |
| PAI 91 SEQ ID NO: 12 | Mpr-V-Har-G-D-W-P-C-NH$_2$ | 0.35 |
| PAI 92 SEQ ID NO: 13 | Mpr-S-Har-G-D-W-P-C-NH$_2$ | 0.24 |
| PAI 93 SEQ ID NO: 14 | Mpr-Har-G-D-W-P-A-C-NH$_2$ | 3.33 |
| PAI 94 SEQ ID NO: 15 | Mpr-Har-G-D-W-P-(N-Me-Ala)-C-NH$_2$ | 1.46 |
| PAI 95 SEQ ID NO: 16 | Mpr-Har-G-D-W-P-G-C-NH$_2$ | 8.66 |
| PAI 96 SEQ ID NO: 17 | Mpr-Har-G-D-W-P-A†-C-NH$_2$ | 0.23 |
| PAI 97 SEQ ID NO: 18 | Mpr-Har-G-D-W-P-P-C-NH$_2$ | 1.40 |
| PAI 98 SEQ ID NO: 19 | Mpr-Har-G-D-W-P-(Sar)-C-NH$_2$ | 0.31 |
| PAI 99 SEQ ID NO: 20 | Mpr-Har-G-D-W-P-(Aib)-Cys-NH$_2$ | 0.46 |
| PAI 100 SEQ ID NO: 21 | Mpr-A-(Har)-G-D-W-P-Pen-NH$_2$ | 0.37 |
| PAI 101 SEQ ID NO: 22 | Mpr-A-K-G-D-W-P-Pen-NH$_2$ | 4.91 |
| PAI 102 | Mpr-D-(Har)-G-D-W-P-Pen-NH$_2$ | 4.04 |

---

I claim:

1. An antibody specifically immunoreactive with a peptide selected from the group consisting of:

| PAI 80 | Mpr-P-Har-G-D-W-P-C-NH$_2$ | (SEQ ID No:1) |
|---|---|---|
| PAI 81 | Mpr-G-Har-G-D-W-P-C-NH$_2$ | (SEQ ID No:2) |
| PAI 82 | Mpr-A-Har-G-D-W-P-C-NH$_2$ | (SEQ ID No:3) |
| PAI 83 | Mpr-Aib-Har-G-D-W-P-C-NH$_2$ | (SEQ ID No:4) |
| PAI 84 | Mpr-(N-Me-Arg)-Har-G-D-W-P-C-NH$_2$ | (SEQ ID No:5) |
| PAI 85 | Mpr-(N-Me-Ser)-Har-G-D-W-P-C-NH$_2$ | (SEQ ID No:6) |
| PAI 86 | Mpr-(D-Ala)-Har-G-D-W-P-C-NH$_2$ | (SEQ ID No:7) |
| PAI 87 | Mpr-(β-Ala)-Har-G-D-W-P-C-NH$_2$ | (SEQ ID No:8) |
| PAI 88 | Mpr-(N-Me-Leu)-Har-G-D-W-P-C-NH$_2$ | (SEQ ID No:9) |
| PAI 89 | Mpr-(N-Me-Ala)-Har-G-D-W-P-C-NH$_2$ | (SEQ ID No:10) |
| PAI 90 | Mpr-Sar-Har-G-D-W-P-C-NH$_2$ | (SEQ ID No:11) |
| PAI 91 | Mpr-V-Har-G-D-W-P-C-NH$_2$ | (SEQ ID No:12) |
| PAI 92 | Mpr-S-Har-G-D-W-P-C-NH$_2$ | (SEQ ID No:13) |
| PAI 93 | Mpr-Har-G-D-W-P-A-C-NH$_2$ | (SEQ ID No:14) |
| PAI 94 | Mpr-Har-G-D-W-P-(N-Me-Ala)-C-NH$_2$ | (SEQ ID No:15) |
| PAI 95 | Mpr-Har-G-D-W-P-G-C-NH$_2$ | (SEQ ID No:16) |
| PAI 96 | Mpr-Har-G-D-W-P-(D-Ala)-C-NH$_2$ | (SEQ ID No:17) |
| PAI 97 | Mpr-Har-G-D-W-P-P-C-NH$_2$ | (SEQ ID No:18) |
| PAI 98 | Mpr-Har-G-D-W-P-(Sar)-C-NH$_2$ | (SEQ ID No:19) |
| PAI 99 | Mpr-Har-G-D-W-P-(Aib)-C-NH$_2$ | (SEQ ID No:20) |
| PAI 100 | Mpr-A-(Har)-G-D-W-P-Pen-NH$_2$ | (SEQ ID No:21) |
| PAI 101 | Mpr-A-K-G-D-W-P-Pen-NH$_2$ | (SEQ ID No:22), and |
| PAI 102 | Mpr-D-(Har)-G-D-W-P-Pen-NH$_2$ | (SEQ ID No:23). |

2. The antibody of claim 1, wherein said peptide is a cyclic peptide comprising a bond between (1) a terminal Mpr and a terminal Cys or (2) a terminal Mpr and a terminal Pen.

3. The antibody of claim 1, wherein said peptide is selected from the group consisting of:

| PAI 84 | Mpr-(N-Me-Arg)-Har-G-D-W-P-C-NH$_2$ | (SEQ ID No:5) |
|---|---|---|
| PAI 85 | Mpr-(N-Me-Ser)-Har-G-D-W-P-C-NH$_2$ | (SEQ ID No:6) |
| PAI 87 | Mpr-(β-Ala)-Har-G-D-W-P-C-NH$_2$ | (SEQ ID No:8) |
| PAI 88 | Mpr-(N-Me-Leu)-Har-G-D-W-P-C-NH$_2$ | (SEQ ID No:9) |
| PAI 89 | Mpr-(N-Me-Ala)-Har-G-D-W-P-C-NH$_2$ | (SEQ ID No:10) |
| PAI 90 | Mpr-Sar-Har-G-D-W-P-C-NH$_2$ | (SEQ ID No:11) |
| PAI 91 | Mpr-V-Har-G-D-W-P-C-NH$_2$ | (SEQ ID No:12) |
| PAI 92 | Mpr-S-Har-G-D-W-P-C-NH$_2$ | (SEQ ID No:13) |
| PAI 93 | Mpr-Har-G-D-W-P-A-C-NH$_2$ | (SEQ ID No:14) |
| PAI 94 | Mpr-Har-G-D-W-P-(N-Me-Ala)-C-NH$_2$ | (SEQ ID No:15) |
| PAI 95 | Mpr-Har-G-D-W-P-G-C-NH$_2$ | (SEQ ID No:16) |
| PAI 96 | Mpr-Har-G-D-W-P-(D-Ala)-C-NH$_2$ | (SEQ ID No:17) |
| PAI 97 | Mpr-Har-G-D-W-P-P-C-NH$_2$ | (SEQ ID No:18) |
| PAI 98 | Mpr-Har-G-D-W-P-(Sar)-C-NH$_2$ | (SEQ ID No:19) |
| PAI 99 | Mpr-Har-G-D-W-P-(Aib)-C-NH$_2$ | (SEQ ID No:20), and |
| PAI 102 | Mpr-D-(Har)-G-D-W-P-Pen-NH$_2$ | (SEQ ID No:23). |

* * * * *